US012558566B2

(12) United States Patent
Gao

(10) Patent No.: US 12,558,566 B2
(45) Date of Patent: Feb. 24, 2026

(54) LIGHT THERAPY DEVICE FOR EYES

(71) Applicant: Guanglang (Hainan) Biotechnology Co., Ltd., Hainan (CN)

(72) Inventor: Te Gao, Hainan (CN)

(73) Assignee: Guanglang (Hainan) Biotechnology Co., Ltd., Haikou (CN)

( * ) Notice: Subject to any disclaimer, the term of this patent is extended or adjusted under 35 U.S.C. 154(b) by 294 days.

(21) Appl. No.: 18/509,296

(22) Filed: Nov. 14, 2023

(65) Prior Publication Data

US 2024/0198129 A1      Jun. 20, 2024

(30) Foreign Application Priority Data

Dec. 19, 2022    (CN) .......................... 202211633043.4

(51) Int. Cl.
*A61N 5/06*              (2006.01)
(52) U.S. Cl.
CPC .... *A61N 5/0622* (2013.01); *A61N 2005/0648* (2013.01); *A61N 2005/0663* (2013.01)
(58) Field of Classification Search
CPC ....................................... A61N 5/06–2005/073
See application file for complete search history.

(56) References Cited

U.S. PATENT DOCUMENTS

| | | | | |
|---|---|---|---|---|
| 5,231,430 | A * | 7/1993 | Kohayakawa | ......... A61B 3/028 351/203 |
| 10,660,182 | B2 * | 5/2020 | Tsubota | ................. H10H 20/80 |
| 2020/0092971 | A1 * | 3/2020 | Tsubota | .................... G09F 9/30 |
| 2024/0226598 | A1 * | 7/2024 | Kushida | ............... A61N 5/0613 |

FOREIGN PATENT DOCUMENTS

CN              115554018 A  *  1/2023  ............... A61F 9/00

* cited by examiner

*Primary Examiner* — Jonathan T Kuo

(57)                    ABSTRACT

A light therapy device for eyes includes a housing and two light channels, where the two light channels are arranged parallel inside the housing and respectively correspond to two eyes of a user; the light channels each are provided therein with a main light source, a light sign slideway, and a moving light sign; an axis of the light channel extends along a line of sight of the eye of the user; the moving light sign is provided between the eye of the user and the main light source; and the moving light sign is connected to an inner wall of the light channel through the light sign slideway. The present disclosure achieves precise positioning of the target position on the retina and precise adjustment of the light intensity on the retina.

10 Claims, 3 Drawing Sheets

LIGHT THERAPY DEVICE FOR EYES

CROSS REFERENCE TO RELATED APPLICATIONS

The present application claims the benefit of Chinese Patent Application No. 202211633043.4 filed on Dec. 19, 2022, the contents of which are incorporated herein by reference in their entirety.

TECHNICAL FIELD

The present disclosure relates to a field of ophthalmic treatment, and in particular to a light therapy device for eyes.

BACKGROUND

With the increasing myopia prevalence year by year, myopia has gradually gained people's attention, and myopia prevention and treatment has gradually entered the public eye. Typically, in myopia prevention and treatment, some devices are used to conduct visual trainings of eyes or simulate light for light irradiation therapy of eyeballs.

In the light irradiation therapy of eyes, the simulated light is usually red light. The incident red light is refracted onto the retina through the lens. After the red light irradiates the retina for a long time, the temperature at the irradiation position increases, thereby promoting blood circulation. However, in the prior art, the distance of the light source and the angle of light irradiation are fixed, so the irradiation position on the retina cannot be adjusted, making it hard to narrow or enlarge the irradiation range. Therefore, the prior art has insufficient flexibility and a single irradiation effect.

SUMMARY

In order to solve the technical problem of non-adjustable irradiation range in the prior art, the present disclosure provides a light therapy device for eyes.

In order to solve the above technical problem, an embodiment of the present disclosure provides a light therapy device for eyes. The light therapy device includes a housing and two light channels, where the two light channels are arranged parallel inside the housing and respectively correspond to two eyes of a user;

the light channels each are provided therein with a main light source, a light sign slideway, and a moving light sign; and an axis of the light channel extends along a line of sight of the eye of the user; the moving light sign is provided between the eye of the user and the main light source; and the moving light sign is connected to an inner wall of the light channel through the light sign slideway.

In a preferred solution, an end of the light channel away from the eye is provided with a plurality of first through-holes; a detachable light shielding cover is provided at a connection position between the housing and the light channel; the light shielding cover is configured to open or close the light channel; and the main light source is connected to the inner wall of the light channel through a fixed rod.

In a preferred solution, the light channel is further provided therein with a light source slideway; and the main light source is connected to the inner wall of the light channel through the light source slideway.

In a preferred solution, the light source slideway and the light sign slideway are electric slideways.

In a preferred solution, the moving light sign is a light-emitting screen with a second through-hole in a center thereof or a light sign plate with a second through-hole in a center thereof.

In a preferred solution, an upper end of the light sign plate is provided with a plurality of fill lights.

In a preferred solution, the light therapy device further includes a control module; and the control module is connected to the main light source, and configured to control a light intensity of the main light source.

In a preferred solution, the light therapy device further includes a power switch, a light source movement switch, and a light sign movement switch; the power switch, the light source movement switch, and the light sign movement switch are connected to the control module; the light sign movement switch includes a light sign forward button and a light sign backward button; and the light source movement switch includes a light source forward button and a light source backward button.

In a preferred solution, the light therapy device further includes a battery module and a charging port; the charging port is provided in the housing and connected to the battery module; and the battery module is configured to provide electrical energy to the light therapy device.

In a preferred solution, the light therapy device further includes a fixing strap and Velcro; the fixing strap is configured to secure a head of the user; and the Velcro is configured to adjust a length of the fixing strap.

Compared with the prior art, the embodiment of the present disclosure has following beneficial effects:

An embodiment of the present disclosure provides a light therapy device for eyes. The light therapy device includes a housing and two light channels, where the two light channels are arranged parallel inside the housing and respectively correspond to two eyes of a user; the light channels each are provided therein with a main light source, a light sign slideway, and a moving light sign; an axis of the light channel extends along a line of sight of the eye of the user; the moving light sign is provided between the eye of the user and the main light source; and the moving light sign is connected to an inner wall of the light channel through the light sign slideway. Compared to the prior art, the present disclosure can change the thickness of the lens of the eye of the user by adjusting the moving light sign, such that the light spot is formed in different ranges on the retina. Therefore, the present disclosure achieves precise positioning of the target position on the retina and precise adjustment of the light intensity on the retina.

Reference Signs: 1. housing; 2. light channel; 21. first through-hole; 3. main light source; 31. fixed rod; 4. moving light sign; 5. light source slideway; 6. light sign slideway; 7. control module; 8. battery module; 9. power switch; 10. light sign movement switch; 11. light source movement switch; 12. fixing strap; 121. Velcro; 13. light shielding cover; 14. eye; 41. fill light; 42. second through-hole; 101. light sign forward button; 102. light sign backward button; 111. light source forward button; 112. light source backward button; 141. lens; 142. retina; 143. choroid; 144. sclera; and 15. charging port.

DETAILED DESCRIPTION

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts should fall within the protection scope of the present disclosure.

Embodiment 1

Figure 1:
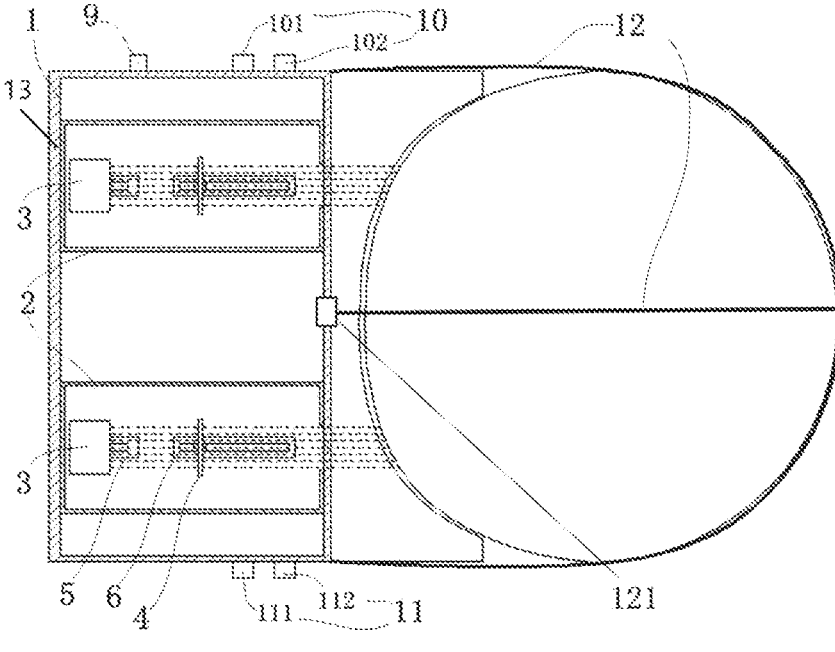
FIG. 1 is a structural diagram of a light therapy device for eyes according to an embodiment of the present disclosure.

Referring to FIG. 1, FIG. 1 shows a light therapy device for eyes 14 provided by an embodiment of the present disclosure.

The light therapy device includes a housing 1 and two light channels 2.

The two light channels 2 are arranged parallel inside the housing 1 and respectively correspond to two eyes of a user.

Figure 2:
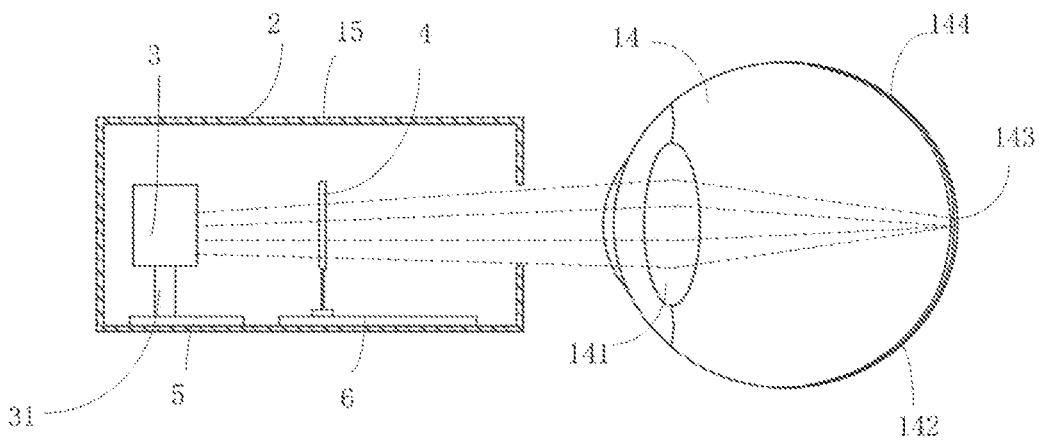
FIG. 2 is a structural diagram of a light channel according to an embodiment of the present disclosure.

Referring to FIG. 2, the light channels 2 each are provided therein with a main light source 3, a light sign slideway 6, and a moving light sign 4.

An axis of the light channel 2 extends along a line of sight of the eye 14 of the user. The moving light sign 4 is provided between the eye 14 of the user and the main light source 3. The moving light sign 4 is connected to an inner wall of the light channel 2 through the light sign slideway 6. In this embodiment, the main light source 3 is configured to provide therapeutic light for the light therapy device, typically red light of a specific wavelength, for example, low-energy high-brightness red light at 630-680 nm. The red light emitted by the main light source 3 is refracted onto a retina 142 through a lens 141. After the red light irradiates the retina 142 for a certain period of time, a temperature at an irradiation position of the retina 142 increases. The temperature is transferred through the retina 142 to a choroid 143 behind to promote blood circulation. Thus, a blood flow rate at the choroid 143 increases, increasing oxygen supply and promoting the growth of a sclera 144. By thickening the sclera 144, a distance between the lens 141 and the retina 142 is changed, achieving the purpose of treating myopia.

Figure 3:
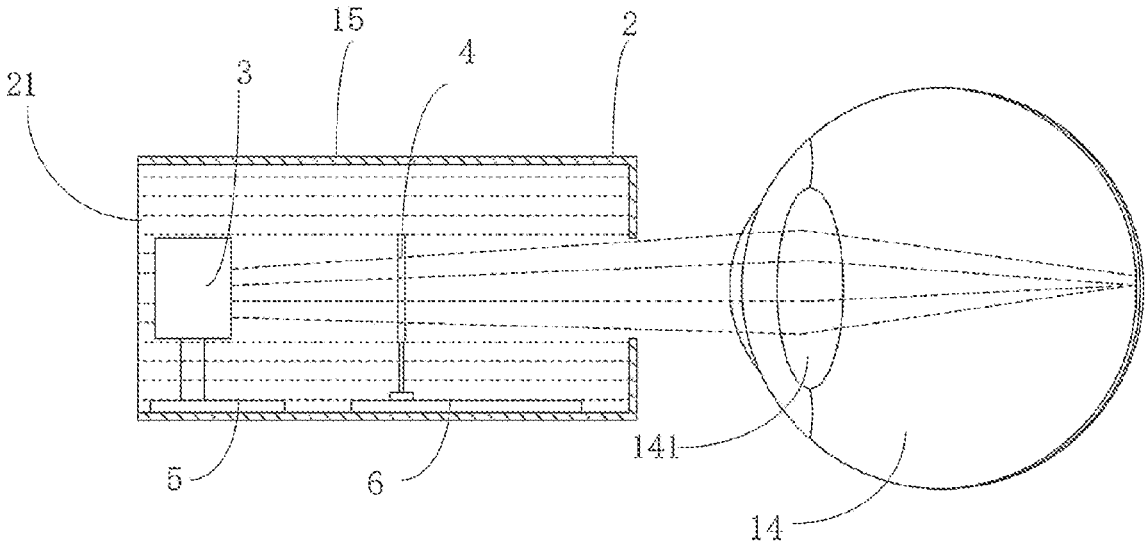
FIG. 3 is a structural diagram of the light channel according to an embodiment of the present disclosure.

Further, in an example of this embodiment, referring to FIGS. 1 and 3, an end of the light channel 2 away from the eye 14 is provided with a plurality of first through-holes 21. A detachable light shielding cover 13 is provided at a connection position between the housing 1 and the light channel 2. The light shielding cover 13 is configured to open or close the light channel 2. The main light source 3 is connected to the inner wall of the light channel 2 through a fixed rod 31. In this example, if there is only the main light source 3 provided in the light channel 2, the light channel 2 will have a black background and may lead to a too large contrast. As a result, prolonged irradiation of the light on the eye 14 of the user may cause discomfort in the eye 14. When the light shielding cover 13 of the light therapy device is removed, natural light is introduced into the light channel 2 through the first through-holes 21. Thus, the irradiation contrast of the main light source 3 is reduced, ensuring comfort of the irradiation treatment process.

In another example of this embodiment, the light channel 2 is further provided therein with a light source slideway 5. The main light source 3 is connected to the inner wall of the light channel 2 through the light source slideway 5. The main light source 3 is connected to the light source slideway 5 through the fixed rod 31. It should be noted that although this embodiment provides examples of two implementations separately, in practical applications, the two implementations can be implemented simultaneously to further expand the adjustment range and improve adjustment flexibility.

In this embodiment, the main light source 3 is provided on the light source slideway 5 in the light channel 2, and is located at the end away from the eye 14 of the user. The moving light sign 4 is provided on the light sign slideway 6 between the eye 14 and the main light source 3. The main light source and the moving light sign can both move back and forth on the light channel 2, in a direction along the axis of the light channel 2. By changing the position of the main light source 3 on the light channel 2 relative to the eye 14 of the user, the size and intensity of a light spot on the retina 142 are changed. By adjusting the moving light sign 4, the moving light sign 4 is moved back and forth relative to the eye 14, and a thickness of the lens 141 changes. Thus, a corresponding focal point of the lens 141 changes, and the light passing through the lens 141 is refracted. Thus, the size and position of the light spot on the retina 142 change, thereby achieving flexible adjustment of the irradiation range. Moreover, by adjusting the position of the moving light sign 4, the focal point of the lens 141 is always in front of the retina 142 to focus the light in front of the retina 142. The design reduces a risk of eye 14 damage caused by long-term, direct irradiation of high-intensity light onto the retina 142. In this example, on the one hand, the main light source 3 can be moved through the light source slideway 5 to change the size and intensity of the light spot on the retina 142. On the other hand, the thickness of the lens 141 of the eye 14 of the user can be changed by adjusting the moving light sign 4, such that the light spot is formed in different ranges on the retina 142. By comprehensively adjusting the positions of the main light source and the moving light sign 4, precise positioning of the target position on the retina 142 and precise adjustment of the light intensity on the retina 142 are achieved.

Figure 4:
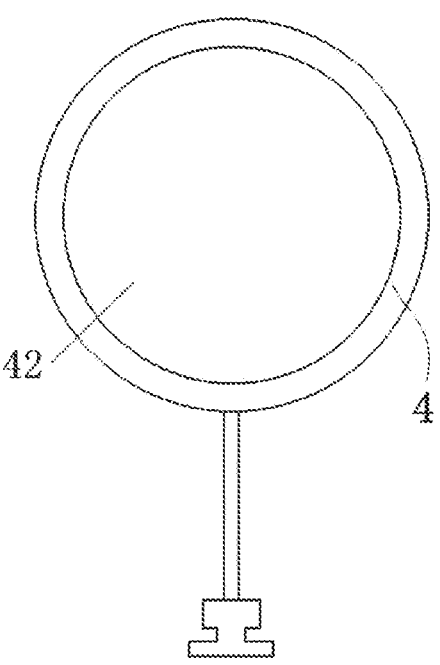
FIG. 4 is a structural diagram of a moving light sign according to an embodiment of the present disclosure.
Figure 5:
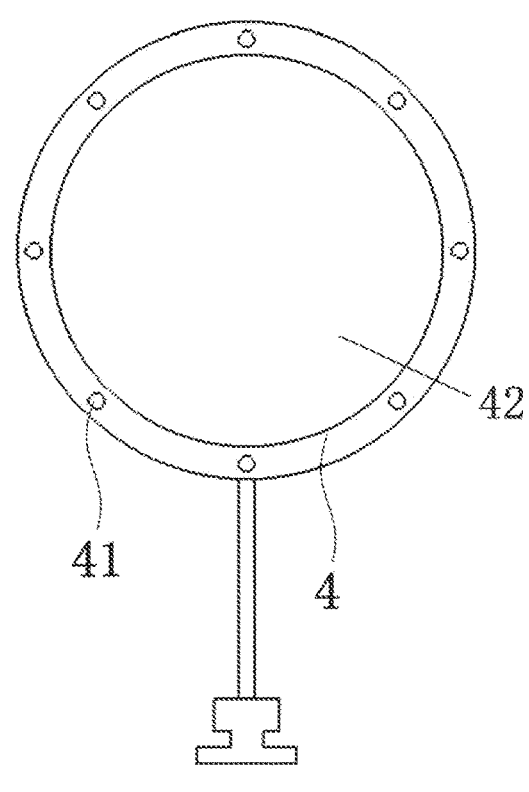
FIG. 5 is a structural diagram of the moving light sign according to an embodiment of the present disclosure.

Further, referring to FIGS. 4 and 5, the moving light sign 4 can be a light-emitting screen with a second through-hole 42 in a center thereof or a light sign plate with a second through-hole 42 in a center thereof. The light emitted by the main light source 3 passes through the second through-hole 42 in the center of the light-emitting screen or the light sign plate, and then passes through a light outlet of the light channel 2 to reach the eye 14 of the user. Preferably, an upper end of the light sign plate is further provided with a plurality of fill lights 41. When the moving light sign 4 is the light-emitting screen, light of the light-emitting screen can be directly adjusted to help the user look at the moving light sign 4, thereby improving the effect of the user's gaze at the second through-hole 42. When the moving light sign 4 is the light sign plate, the fill lights 41 are controlled to adjust illumination light, so as to help the user look at the moving light sign 4.

Figure 6:
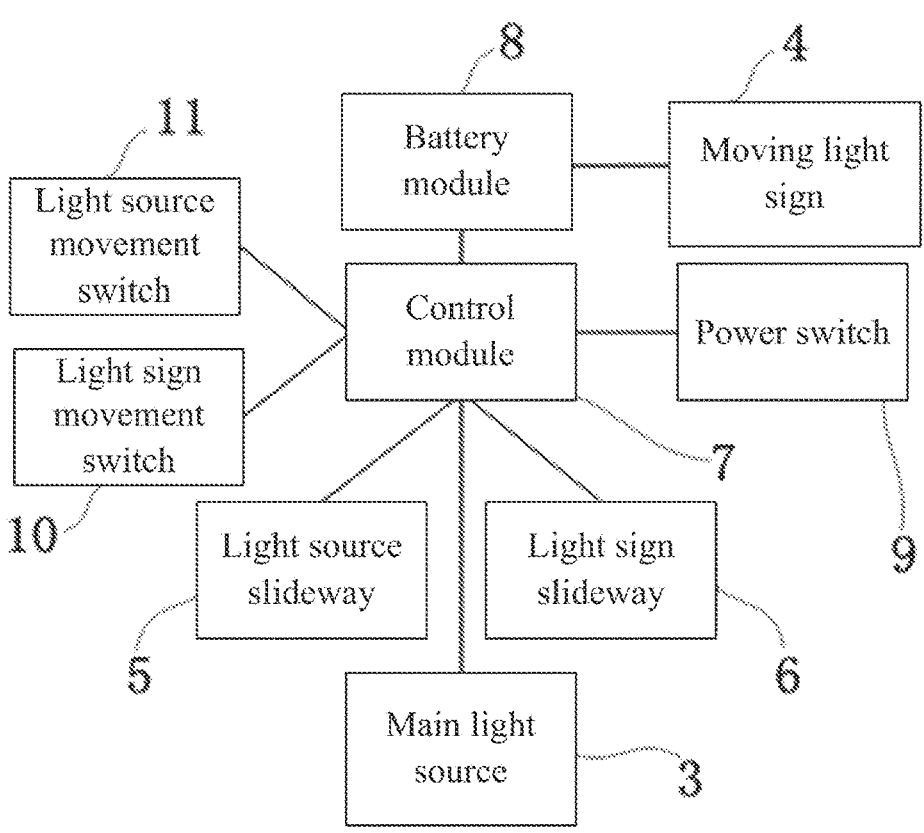
FIG. 6 is a block diagram of the light therapy device for eyes according to an embodiment of the present disclosure.

In a preferred implementation, referring to FIG. 6, the light therapy device further includes a control module 7. The control module 7 is connected to the main light source 3, and configured to control a light intensity of the main light source 3.

The control module 7 may include a microcontroller unit (MCU), a resistor, a capacitor, an inductor, and an interface device.

The light therapy device further includes a battery module 8 and a charging port 15. The charging port 15 is provided in the housing 1 and connected to the battery module 8. The battery module 8 is configured to provide electrical energy to the light therapy device (for example, to power the main light source 3 and the moving light sign 4).

Further, the light source slideway 5 and the light sign slideway 6 are electric slideways. The light source slideway 5 and the light sign slideway 6 are connected to the control module 7. Therefore, the electric slideways are controlled through the control module 7. Compared to manual adjustment in the prior art, the present disclosure can effectively control the positions of the main light source 3 and the moving light sign 4 relative to the eye 14 of the user, thereby improving control accuracy.

Preferably, the light therapy device further includes a power switch 9, a light source movement switch 11, and a light sign movement switch 10. The power switch 9, the light source movement switch 11, and the light sign movement switch 10 are connected to the control module 7. The power switch 9 serves as a main switch of the light therapy device, and configured to control an overall working state of the light therapy device. The light sign movement switch 10 includes a light sign forward button 101 and a light sign backward button 102. The light source movement switch 11 includes a light source forward button 111 and a light source backward button 112. The light sign forward button 101 and the light sign backward button 102 are configured to send commands of moving the moving light sign 4 forward and backward to the control module 7, so as to control the light sign slideway 6 to move the moving light sign 4 forward and backward. The light source forward button 111 and the light source backward button 112 are configured to send commands of moving the main light source 3 forward and backward to the control module 7, so as to control the light source slideway 5 to move the main light source 3 forward and backward.

It should be noted that in the light therapy device, the power switch 9, the light source movement switch 11, and the light sign movement switch 10 are connected to the control module 7. The main light source 3 is connected to the control module 7. The light source slideway 5 and the light sign slideway 6 are connected to the control module 7. The moving light sign 4 is directly connected to the battery module 8. It should be noted that control module 7 is connected to the light sign slideway 6, while the moving light sign 4 is connected to the battery module 8. In other words, the control of the movement of the light sign slideway 6 and the control of the illumination light of the moving light sign 4 (if the moving light sign 4 is a light-emitting screen, it directly emits the illumination light, and if the moving light sign 4 is a light sign plate, the fill lights 41 at the upper end of the light sign plate emit the illumination light) are independent of each other.

In this embodiment, the light therapy device further includes a fixing strap 12 and Velcro 121. The fixing strap 12 is configured to secure a head of the user. The Velcro 121 is configured to adjust a length of the fixing strap 12 to meet different size requirements and adapt to the light therapy device. Specifically, the fixing strap 12 can be made of an elastic material to enhance user comfort. Two ends of the fixing strap 12 are provided with the Velcro 121. Correspondingly, the housing 1 is further provided with Velcro. When light therapy is performed for the user, the Velcro at the ends of the fixing strap 12 is attached to the Velcro on the housing 1, thereby achieving effective fixation.

Compared with the prior art, the embodiment of the present disclosure has following beneficial effects:

An embodiment of the present disclosure provides a light therapy device for eyes. The light therapy device includes a housing and two light channels, where the two light channels are arranged parallel inside the housing and respectively correspond to two eyes of a user; the light channels each are provided therein with a main light source, a light sign slideway, and a moving light sign; an axis of the light channel extends along a line of sight of the eye of the user; the moving light sign is provided between the eye of the user and the main light source; and the moving light sign is connected to an inner wall of the light channel through the light sign slideway. Compared to the prior art, the present disclosure can change the thickness of the lens of the eye of the user by adjusting the moving light sign, such that the light spot is formed in different ranges on the retina. Therefore, the present disclosure achieves precise positioning of the target position on the retina and precise adjustment of the light intensity on the retina.

The objectives, technical solutions, and beneficial effects of the present disclosure are further described in detail through the above specific embodiments. It should be understood that the above are merely some specific embodiments of the present disclosure, but are not intended to limit the protection scope of the present disclosure. It should be particularly noted that, any modifications, equivalent substitutions, improvements, and the like made by those skilled in the art within the spirit and principle of the present disclosure should be included within the protection scope of the present disclosure.

The invention claimed is:

1. A light therapy device for eyes, comprising a housing and two light channels, wherein the two light channels are arranged parallel inside the housing and respectively correspond to two eyes of a user;

the light channels each are provided therein with a main light source, a light sign slideway, and a moving light sign; and an axis of the light channel extends along a line of sight of the eye of the user; the moving light sign is provided between the eye of the user and the main light source; and the moving light sign is connected to an inner wall of the light channel through the light sign slideway.

2. The light therapy device for eyes according to claim 1, wherein an end of the light channel away from the eye is provided with a plurality of first through-holes; a detachable light shielding cover is provided at a connection position between the housing and the light channel; the light shielding cover is configured to open or close the light channel; and the main light source is connected to the inner wall of the light channel through a fixed rod.

3. The light therapy device for eyes according to claim 1, wherein the light channel is further provided therein with a light source slideway; and the main light source is connected to the inner wall of the light channel through the light source slideway.

4. The light therapy device for eyes according to claim 3, wherein the light source slideway and the light sign slideway are electric slideways.

5. The light therapy device for eyes according to claim 4, further comprising a control module, wherein the control module is connected to the main light source, and configured to control a light intensity of the main light source.

6. The light therapy device for eyes according to claim 5, further comprising a power switch, a light source movement switch, and a light sign movement switch, wherein the power switch, the light source movement switch, and the light sign movement switch are connected to the control module; the light sign movement switch comprises a light sign forward button and a light sign backward button; and the light source movement switch comprises a light source forward button and a light source backward button.

7. The light therapy device for eyes according to claim 1, wherein the moving light sign is a light-emitting screen with a second through-hole in a center thereof or a light sign plate with a second through-hole in a center thereof.

8. The light therapy device for eyes according to claim 7, wherein an upper end of the light sign plate is provided with a plurality of fill lights.

9. The light therapy device for eyes according to claim 1, further comprising a battery module and a charging port, wherein the charging port is provided on the housing and connected to the battery module; and the battery module is configured to provide electrical energy to the light therapy device.

10. The light therapy device for eyes according to claim 1, further comprising a fixing strap and Velcro, wherein the fixing strap is configured to secure a head of the user; and the Velcro is configured to adjust a length of the fixing strap.

\* \* \* \* \*